(12) United States Patent
Carroll et al.

(10) Patent No.: US 6,706,536 B1
(45) Date of Patent: Mar. 16, 2004

(54) METHOD AND APPARATUS FOR PROCESSING COAGULATION STUDIES, CHEMISTRY PROCEDURES AND THE LIKE

(75) Inventors: Wallace E. Carroll, Santa Barbara, CA (US); R. David Jackson, Rio Rancho, NM (US)

(73) Assignee: WADA, Inc., Santa Barbara, CA (US)

( * ) Notice: Subject to any disclaimer, the term of this patent is extended or adjusted under 35 U.S.C. 154(b) by 280 days.

(21) Appl. No.: 09/724,529

(22) Filed: Nov. 28, 2000

(51) Int. Cl.⁷ .............................................. G01N 21/00
(52) U.S. Cl. ........................ 436/164; 436/43; 436/45; 436/47; 436/54; 436/171; 436/69; 422/72
(58) Field of Search ............................ 436/45, 48, 81, 436/47, 180, 43; 422/106, 72, 67; 210/745

(56) References Cited

U.S. PATENT DOCUMENTS

| | | |
|---|---|---|
| 3,458,287 A | 7/1969 | Gross et al. |
| 3,593,568 A | 7/1971 | Schmitz |
| 3,905,769 A | 9/1975 | Carroll et al. |
| 3,920,549 A | 11/1975 | Gigliello et al. |
| 4,049,692 A | 9/1977 | Zine, Jr. |
| 4,071,316 A | 1/1978 | Wright |
| 4,217,107 A | 8/1980 | Saito et al. |
| 4,279,616 A | 7/1981 | Saito et al. |
| 4,720,787 A | 1/1988 | Lipscomb |
| 4,788,139 A | 11/1988 | Ryan |
| 4,917,801 A * | 4/1990 | Luderer et al. ............. 210/516 |
| 4,927,545 A * | 5/1990 | Roginski .................... 210/745 |
| 5,156,974 A | 10/1992 | Grossman et al. |
| 5,188,940 A | 2/1993 | Krause et al. |
| 5,197,017 A | 3/1993 | Carroll et al. |
| 5,502,651 A | 3/1996 | Jackson et al. |
| 5,526,111 A | 6/1996 | Collins et al. |
| 5,981,285 A | 11/1999 | Carroll et al. |

OTHER PUBLICATIONS

Product literature entitled "Can the color of a blood collection tube make a difference in patent care?", Becton Dickinson, 1996.

Product literature entitled "The progress goes on" Sarsted, Inc.

Article entitled "A Simple, Graphical Method to Evaluate Laboratory Assays" Jan S. Krouwer and Katherine L. Monti, Eur. J. Clin. Chem. Clin. Biochem. 1995; 33 (No. 8), pp. 925–927.

Article entitled "The Reliability of Manufacturer–determined, instrument–specific International Sensitivity Index Values for Calculating the International Normalized Ratio" Mark T. Cunningham et al., A.J.C.P. Jul. 1994, vol. 102, No. 1, pp. 128–133.

(List continued on next page.)

*Primary Examiner*—Jill Warden
*Assistant Examiner*—Sam P. Siefke
(74) *Attorney, Agent, or Firm*—John F. A. Earley; John F. A. Earley, III; Harding, Earley, Follmer & Frailey

(57) ABSTRACT

A method and apparatus for processing coagulation studies, chemistry procedures and the like, the apparatus including a container having a space for containing a body fluid sample therein, a covered opening and being provided with optically clear sides and a uniform cross-sectional configuration over at least a portion of the container, the cover being pierceable to permit the selective addition of reagents to be delivered into the container space, and the apparatus and method facilitating carrying out analytical procedures on body fluid sample when it is contained in the container. The apparatus further including instrumentation for optically reading and analyzing the fluid sample and adding appropriate reagents while the sample it is in the container.

34 Claims, 3 Drawing Sheets

OTHER PUBLICATIONS

Article entitled "Oral Anticoagulants Mechanism of Action, Clinical Effectiveness, and Optimal Therapeutic Range" Jack Hirsh et al., Chest/102/4/Oct., 1992/Supplement, pp. 312S–326S.

Article entitled "Reliability and Clinical Impact of the Normalization of the Prothrombin Times in Oral Anticoagulant Control" E.A. Loeliger and S.M. Lewis, Thrombosis and Heamostasis—F.K. Schattauer Verlag GmbH (1985), pp. 148–154.

Article entitled "Highly Sensitive Thromboplastins Do Not Improve INR Precision" Valerie L. Ng, et al., A.J.C.P., Mar. 1998, vol. 109, No. 3, pp. 338–346.

Article entitled "Pts, Prs, ISIs, and INRs: A Primer on Prothrombin Time Reporting Part I: Calibration of Thromboplastin Reagents and Principles of Prothrombin Time Reporting" Ray F. Ebert, Ph D, Clinical Hemostasis Review, Nov. 1993.

Article entitled "Rapid Ribrinogen Determination with the Prothrombin time using a Potentiophotometer" W.E. Carroll and R.D. Jackson, Research Communications in Molecular Pathology and Pharmacology, vol. 89, No. 1, 1995.

Article entitled "Fibrinogen Determinations: An Automated Photoelectric System" A.B. Glassman et al., The American Society of Clinical Pathologiests, Spring Meeting, Feb. 1972, Atlanta, Georgia.

Article entitled, "Rapid Determination of Fibrinogen by Thrombokinetics" Ethan A. Natelson and Denise F. Dooley, A.J.C.P., vol. 61 Jun. 1974, pp. 828–833.

Article entitled "Markers of in vivo activation of coagulation interrelationships change with intensity of oral anticoagulation" Susan Solymoss and Edwin G. Bovill, A.J.C.P. Mar. 1996, vol. 105, No. 3, pp. 293–297.

Article entitled "Baxter Diagnostics Inc. Dade Determination of INR (International Normalized Ratio) Values using Dade Calibrated Innovin" Baxter Diagnostics, Inc. Aug. 1994.

Article entitled "Accuracy of Laboratory adn Portable Monitor International Normalized Ratio Determinations" Scott Kaatz et al. Arch Intern Med/vol. 155, Sep. 25, 1995, pp. 1861–1867.

Article entitled "Minimum Lyophilized Plasma Requirement for ISI Calibration" Leon Pollers, et al., A.J.C.P. Feb. 1998, vol. 109, No. 2, pp. 196–204.

Paper entitled "The Significance for Platelet Counts in Coagulation Studies" W.E. Carroll et al., Department of Pathology, Santa Barbara Cottage Hospital, Sansum Medical Research Institute, Jan. 2001.

Product literature entitled "Greiner Unbreakable Plastic Tubes" Greiner Vacuette North America, Feb. 2, 2000.

Article entitled "Modified Anticoagulant therapy factor and International Normalized Ratio in Patients in an unstable coagulation state with respect to warfarin therapy" W.E. Carroll and R.D. Jackson, Research Communications in molecular pathology and pharmacology, 1999, vol. 105, No. 3, pp. 262–270.

Product literature entitled "Tube Guide Vacutainer with Hemogard Closure" Becton Dickinson, 1990.

Product literature entitled "Order of draw for multiple tube collections" Becton Dickinson, 1995.

Product literature entitled "Successful specimen collection: finger puncture" Becton Dickson, 1996.

Product literature entitled "Phlebotomy update—important information for collecting small–volume blood samples" Becton Dickson, 1994.

Product literature entitled "A engineering control for safer blood–specimen handling" Becton Dickinson, 1994.

Product literature entitled "Attention: Becton Dickinson is adjusting label designs to provide greater distinction between 3.2% solution and other sodium citrate solution tubes" Becton Dickinson, 1997.

Article entitled Baxter Diagnostics Inc. Dade Determination of INR (International Normalized Ratio) Values using Dade calibrated thromboplastin, Baxter Diagnostics, Inc., 1991.

Article entitled "Accuracy and Precision of the CoaguCheck System in the Outpatient Setting" Judy R. Bodwell, Senior Clinical Research Associate, Boehringer Mannheim Corporation.

Article entitled "Special Report: A Simple System for the Derivation of International Normalized Ratios for the Reporting of Prothrombin Time Results with North American Thromboplastin Reagents", Leon Poller, D.Sc., and Jack Hirsh, M.D., Award Articles and Special Reports, vol. 92, No. 1, pp. 124–126.

Article entitled "Accuracy of Laboratory and Portable Monitor International Normalized Ratio Determinations", Scott S. Kaatz, Do; et al., Arch Intern Med/vol. 155, Sep. 25, 1995, pp. 1861–1867.

Article entitled "Minimum Lyophilized Plasma Requirement for ISI Calibration", Leon Poller, DSc, et al., Coagualtion and Transfusion Medicine, AJCP, Feb. 1998, vol. 109, No. 2, pp. 196–204.

Product information entitled "Dade Thromboplastin C Plus", Dade Behring, Jan. 1999 (also enclosed is the Spainish version).

Product information entitled "Dade Determination of INR (International Normalized Ratio)", Dade Behring, Jun. 1999.

Product information entitled "Dade Determination of INR (International Normalized Ratio) Values using Dade Calibrated Innovin", Baxter Diagnostics Inc., Revised 8/94.

Product information entitled "Dade Thromboplastin C Plus Dried Rabbit Btrain Thromboplastin with Calcuim", Baxter Diagnostics Inc., Revised 4/95.

Product information entitled "Dade Innovin Dried recombinant human tissue factor with calcuim", Baxter Diagnostics Inc., Revised 8/94.

Product information entitled "Dade Determination of INR Values using Dade Calibrated Thromboplastin", Baxter Diagnostics Inc., Revised 2/93.

* cited by examiner

METHOD AND APPARATUS FOR PROCESSING COAGULATION STUDIES, CHEMISTRY PROCEDURES AND THE LIKE

BACKGROUND OF THE INVENTION

1. Field of the Invention

This invention relates to the field of devices useful for containing and analyzing blood for carrying out coagulation studies and other chemistry procedures, and a method for carrying out the procedures, including monitoring oral anticoagulant therapy to take into account the platelet count in determining prothrombin times (PT), International Normalized Ratios (INR), and partial thromboplastin times (PT).

2. Description of the Prior Art

Handling of human blood and body fluids in open containers carries with it the potential danger of the transmission of HIV (AIDS), Hepatitis B, Hepatitis C and other blood-borne diseases. It is desirable to avoid all human contact with blood. Existing coagulation and chemistry systems have capped holders for the blood which commonly comprise a stoppered tube containing a vacuum therein. One such example of a vacuum tube is the VACUTAINER® (Becton Dickinson). A needle apparatus is used in connection with the container to aspirate a fixed, known quantity of blood or blood plasma by piercing the container cap. The quantity of blood or plasma is then dispensed into open cuvettes where reactions take place. Automatic methods exist to dispose of the spent reactant cuvettes, but the cuvettes, too, are open. This open system has the potential for exposing blood to medical personnel.

In carrying out analyses of human blood, there exist certain inherent risks to those individuals, in particular, medical personnel, who handle the blood containers. The blood borne diseases, if not contained, can be deleterious to the health of those coming into contact with the blood. Blood is generally sampled from humans using a syringe and needle. The needle is inserted into a blood vessel or a catheter through which blood is withdrawn. It is the common practice to withdraw the blood through the needle and deliver the blood from the needle into a sample tube in which the blood can be temporarily stored for transport to the lab.

It is a common practice for a lab technician to remove blood from a sample tube, such as a cuvette, and then perform the appropriate analyses on the blood sample. Often, the testing involves mixing the blood with reagents, and undertaking studies of transformation of blood components, and production of components from enzymes. When the blood tube is opened, or when blood is removed from the tube, there is a risk of spilling the blood, or a risk of human contact with the blood. While medical personnel attempt to guard against these risks by wearing protective gear, such as gloves, face shields, lab coats, and other coverings, the risk of spillage remains. Furthermore, in some cases, due to the cumbersome coverings, gloves, lab coats, shields, and the like, carrying out testing is impeded, and sometimes, the protective coverings worn by individuals must be removed, and then replaced.

While robotics have been employed to facilitate processing of a blood sample. It is known to withdraw blood into a sample container or vial and store the container with one or more other samples, for processing, where a robotic arm is used to withdraw an amount of fluid from the sample vial and transfer that amount to a second vial for further processing. In some cases, the sample contents are transferred from a second vial to yet a third vial for spectrophotometic analysis. The original fluid sample is therefore removed from a container and the risks of handling and spillage, even though done with a robotic apparatus, still have the potential to contaminate the environment outside of the original sample vial.

Similarly, disposal of open containers presents a further problem. Risks of human contact with blood and other body fluids are present during the disposal, since the open container holding the blood sample must be handled, or the blood or fluid sample which has been removed from a closed tube disposed of properly.

A need exists for an apparatus and device which reduces the risk of contacting blood, but at the same time permits test analyses to be carried out. The present invention provides a novel apparatus and method for containing blood at the point of its withdrawal from a source, and up to and throughout its testing, then disposal.

Testing of blood and other body fluids is commonly done in hospitals, labs, clinics and other medical facilities. For example, to prevent excessive bleeding or deleterious blood clots, a patient may receive oral anticoagulant therapy before, during and after surgery. To assure that the oral anticoagulant therapy is properly administered, strict monitoring is accomplished and is more fully described in various medical technical literature, such as the articles entitled "PTs, PR, ISIs and INRs: A Primer on Prothrombin Time Reporting Parts I and II" respectively published November, 1993 and December, 1993 issues of *Clinical Hemostasis Review*, and herein incorporated by reference.

These technical articles disclose anticoagulant therapy monitoring that takes into account three parameters which are: International Normalized Ratio (INR), International Sensitivity Index (ISI) and prothrombin time (PT), reported in seconds. The prothrombin time (PT) indicates the level of prothrombin and blood factors V, VII, and X in a plasma sample and is a measure of the coagulation response of a patient. The INR and ISI parameters are needed so as to take into account various differences in instrumentation, methodologies and in thromboplastins' (Tps) sensitivities used in anticoagulant therapy. In general, thromboplastins (Tps) used in North America are derived from rabbit brain, those previously used in Great Britain from human brain, and those used in Europe from either rabbit brain or bovine brain. The INR and ISI parameters take into account all of these various different factors, such as the differences in thromboplastins (Tps), to provide a standardized system for monitoring oral anticoagulant therapy to reduce serious problems related to prior, during and after surgery, such as excessive bleeding or the formation of blood clots.

As reported in Part I (Calibration of Thromboplastin Reagents and Principles of Prothrombin Time Report) of the above technical article of the *Clinical Hemostasis Review*, the determination of the INR and ISI parameters are quite involved, and as reported in Part II (Limitation of INR Reporting) of the above technical article of the *Clinical Hemostasis Review*, the error yielded by the INR and ISI parameters is quite high, such as about 13%. The complexity of the interrelationship between the International Normalized Ratio (INR), the International Sensitivity Index (ISI) and the patient's prothrombin time (PT) may be given by the below expression (1), wherein the quantity $$\left[\frac{\text{Patient's } PT}{\text{Mean of } PT \text{ Normal Range}}\right]$$

is commonly referred to as prothrombin ratio (PR):

$$INR = \left[\frac{\text{Patient's } PT}{\text{Mean of } PT \text{ Normal Range}}\right]^{ISI} \quad (1)$$

The possible error involved with the use of International Normalized Ratio (INR) is also discussed in the technical article entitled "Reliability and Clinical Impact of the Normalization of the Prothrombin Times in Oral Anticoagulant Control" of E. A. Loeliger et al, published in *Thrombosis and Hemostasis* 1985; 53: 148–154, and herein incorporated by reference. As can be seen in expression (1), ISI is an exponent of INR which leads to the possible error involved in the use of INR to be about ±13.5% or possibly even more. A procedure related to the calibration of the ISI is described in a technical article entitled "Failure of the International Normalized Ratio to Generate Consistent Results within a. Local Medical Community" of V. L. Ng et al, published in Am. J. Clin Pathol 1993; 99: 689–694, and herein incorporated by reference.

The unwanted INR deviations are further discussed in the technical article entitled "Minimum Lyophilized Plasma Requirement for ISI Calibration" of L. Poller et al published in *Am J Clin Pathol* February 1998, Vol. 109, No. 2, 196–204, and herein incorporated by reference. As discussed in this article, the INR deviations became prominent when the number of abnormal samples being tested therein was reduced to fewer than 20 which leads to keeping the population of the samples to at least 20. The paper of L. Poller et al also discusses the usage of 20 high lyophilized INR plasmas and 7 normal lyophilized plasmas to calibrate the INR. Further, in this article, a deviation of +/−10% from means was discussed as being an acceptable limit of INR deviation. Further still, this article discusses the evaluation techniques of taking into account the prothrombin ratio (PR) and the mean normal prothrombin time (MNPT), i.e., the geometric mean of normal plasma samples.

The discrepancies related to the use of the INR are further studied and described in the technical article of V. L. NG et al entitled, "Highly Sensitive Thromboplastins Do Not Improve INR Precision," published in *American Journal of Clinical Pathology*, 1998; 109, No. 3, 338–346 and herein incorporated by reference. In this article, the clinical significance of INR discordance is examined with the results being tabulated in Table 4 therein and which are analyzed to conclude that the level of discordance for paired values of individual specimens tested with different thromboplastins disadvantageously range from 17% to 29%.

U.S. Pat. No. 5,981,285 issued on Nov. 9, 1999 to Wallace E. Carroll et al., which discloses a "Method and Apparatus for Determining Anticoagulant Therapy Factors" provides an accurate method for taking into account varying prothrombin (PT) times caused by different sensitivities of various thromboplastin formed from rabbit brain, bovine brain or other sources used for anticoagulant therapy. This method does not suffer from the relatively high (13%) error sometimes occurring because of the use of the INR and ISI parameters with the exponents used in their determination.

This invention relates to the inventions disclosed in U.S. Pat. Nos. 3,905,769 ('769) of Sep. 16, 1975; U.S. Pat. No. 5,197,017 ('017) dated Mar. 23, 1993; and U.S. Pat. No. 5,502,651 ('651) dated Mar. 26, 1996, all issued to Wallace E. Carroll and R. David Jackson, and all of which are incorporated herein by reference. The present invention provides an apparatus for containing and carrying out reactions and analyses on blood and other body fluids. The invention has particular utility for monitoring anticoagulant therapy, as well as other blood and fluid analyses.

SUMMARY OF THE INVENTION

The method and apparatus according to the present invention are useful for processing coagulation studies, and other chemistry procedures involving blood or other body fluids. The apparatus and method, in accordance with a preferred embodiment of the present invention, are used to determine anticoagulant therapy factors which are designated herein, in particular, prothrombin times (PT), International Normalized Ratios (INR) and modified ATF (MATF), corrected ATF (CATF) and are dependent on the prothrombin time (PT), the prothrombin ratio (PR), a fibrinogen transformation rate (FTR), and a maximum acceleration point (MAP) having an associated time to maximum acceleration (TMA). The anticoagulant therapy factors' rates comprise a predetermined range starting prior to and ending after a maximum acceleration point which corresponds to the maximum acceleration of the fibrinogen (FBG) to fibrin conversion.

A further object of the present invention is to provide a method and apparatus for carrying out analyses to obtain corrected ATF (CATF) and modified ATF (MATF) values.

In accordance with the present invention, there is provided an apparatus and method for containing fluids, such as blood and other body fluids, and processing the fluids to carry out coagulation studies and other chemical procedures and analyses. A container device is provided which can receive and contain fluid from the point of withdrawal, from a body, contain the fluid throughout the processing and testing procedures and can be disposed of with the fluid after testing has been completed. In a preferred embodiment of the invention, the container means is a container having optically clear sides surrounding the container space, with a cover sealing off an opening of the container, and a reagent within the sealed container space, such as an anticoagulant reagent.

In carrying out coagulation studies it is important to isolate red blood cells (and white blood cells and platelets) from plasma. The device constructed in accordance with a preferred embodiment of the present invention is useful for coagulation studies. For example, a device constructed in accordance with the present invention is provided to receive and hold withdrawn blood as well as reagents. The separation of plasma and red blood cell components can be accomplished without removing the blood from the container.

Further, the invention provides a monitoring system for monitoring the blood and its components, along with reagents and other material contained in the sample container of the present invention. A computer is provided to store and integrate data collected by the monitoring system. The monitoring system, in accordance with a preferred embodiment of the present invention, has an optical emitter and a photo cell for taking spectropotentiophotometric readings of the contents of the sample container.

It is an object of the present invention to provide an apparatus for containing a body fluid such as blood, from the point of withdrawal of a body and during chemical processing and analyses so that removal of blood from the container is not necessary.

It is another object of the present invention to accomplish the above object by providing an optical reading device for determining optical measurements associated with blood and fluid samples while the blood and fluid samples are contained in the sample container into which they were originally drawn.

It is another object of the present invention to provide a sample container which has a chemical contained therein and can receive and contain a sample of fluid withdrawn from a body.

It is another object of the present invention to accomplish the above object where the chemical contained in the container is a blood preserving chemical.

It is another object of the present invention to provide an apparatus for analyzing blood and fluids as they sit in a sample container into which the blood and fluid were originally sampled from a body.

It is another object of the present invention to provide a method for carrying out blood analysis where fluid, such as blood, is withdrawn from its source (i.e., a human body), into a container device where it remains throughout testing and analysis and disposal.

It is another object of the present invention to provide a method and apparatus for carrying out coagulation studies and other chemical processes, where the fluid being studied and analyzed is permitted to remain in the apparatus from the time of its withdrawal, throughout testing and analysis, and when disposed of.

It is another object of the present invention to provide a novel method and apparatus for handling and processing blood and other body fluids which has improved safety features that reduce the risk of contact with the blood and fluids by medical personnel.

It is another object of the present invention to provide a novel method and apparatus useful for monitoring anticoagulant therapy.

It is another object of the present invention to carry out the above objects where the apparatus contains a silicone compound and an anticoagulant buffer predisposed in the apparatus for contact with fluid to be contained therein.

It is another object of the present invention to accomplish the above objects by providing a container device having a sealable opening which prevents container contents from exiting the container but permits the selective entry of reagents and other compounds into the container.

DETAILED DESCRIPTION

Figure 1:
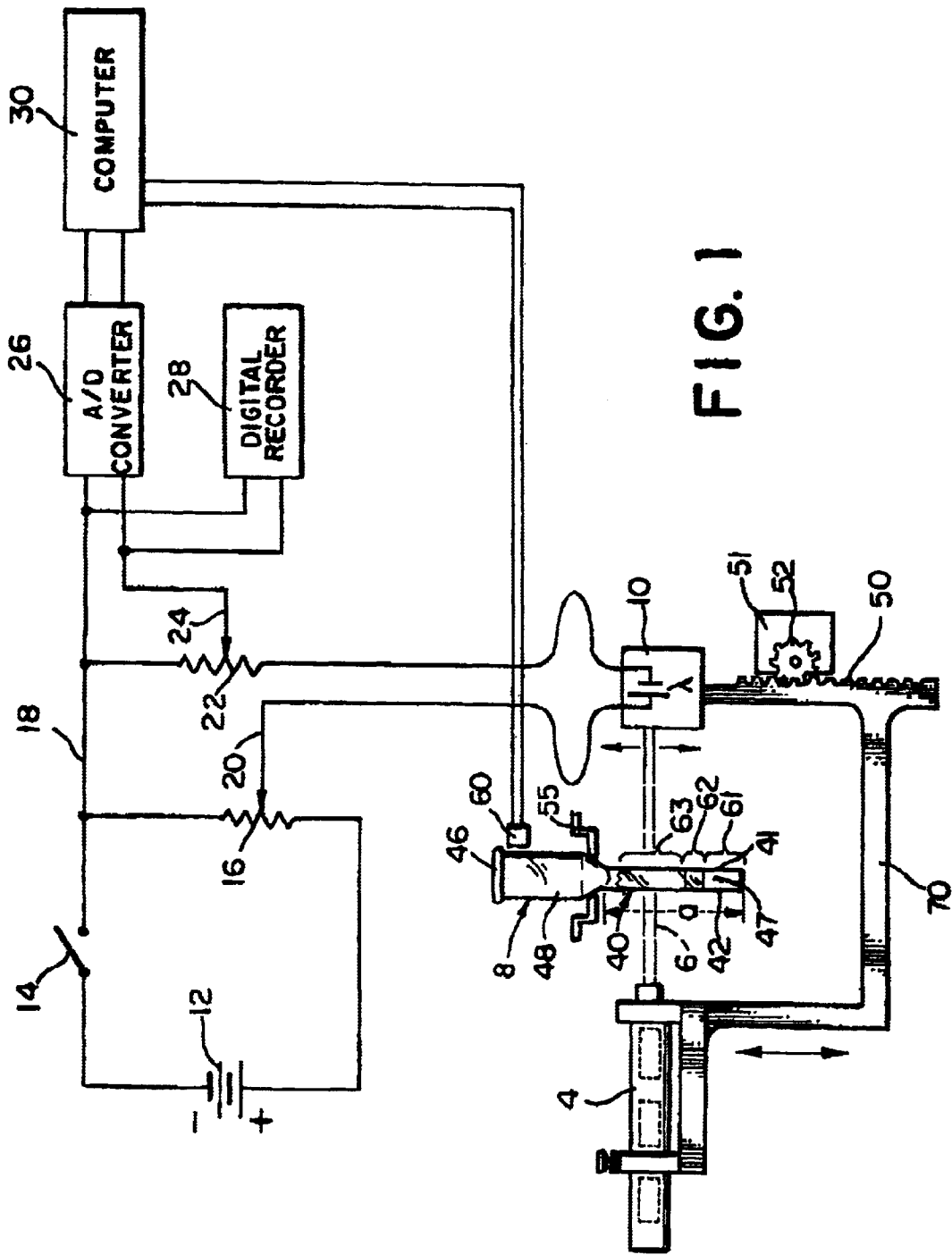
FIG. 1 is a diagram of potentiophotometric apparatus constructed in accordance with the present invention for determining blood chemistry analyses such as coagulation studies, including anticoagulant therapy factor (ATF) determination, where the output of the analog/digital (A/D) converter is applied to a computer.

Referring to the drawings, wherein the same reference numbers indicate the same elements throughout, there is shown in FIG. 1 a light source 4 which may be a low power gas laser, or other light producing device, producing a beam of light 6 which passes through a sample test tube, such as the container 8, and is received by detection means which is preferably a silicon or selenium generating photocell 10 (photovoltaic cell). Battery 12 acts as a constant voltage DC source. Its negative terminal is connected through switch 14 to one end of variable resistor 16 and its positive terminal is connected directly to the opposite end of variable resistor 16. The combination of battery 12 and variable resistor 16 provides a variable DC voltage source, the variable voltage being derivable between line 18 at the upper terminal of resistor 16 and wiper 20. This variable DC voltage source is connected in series with detection means photocell 10, the positive output of detection means photocell 10 being connected to the wiper 20 of variable resistor 16 so that the voltage produced by the variable voltage DC source opposes the voltage produced by the detection means photocell 10. The negative output of detection means photocell 10 is connected through variable resistor 22 to line 18. Thus, the voltage across variable resistor 22 is the difference between the voltage produced by the variable voltage DC source and the voltage produced by the photovoltaic cell 10. The output of the electrical network is taken between line 18 and wiper 24 of variable resistor 22. Thus, variable resistor 22 acts as a multiplier, multiplying the voltage produced as a result of the aforesaid subtraction by a selective variable depending on the setting of variable resistor 22. The potentiophotometer just described embodies the electrical-analog solution to Beer's Law and its output is expressed directly in the concentration of the substance being measured.

In the present invention, wiper 24 is placed at a position to give a suitable output and is not varied during the running of the test. The output between line 18 and wiper 24 is delivered to an A/D converter 26 and digital recorder 28. As is known, the A/D converter 26 and the digital recorder 28 may be combined into one piece of equipment and may, for example, be a device sold commercially by National Instrument of Austin, Texas as their type Lab-PC+. The signal across variable resistor 22 is an analog signal and hence the portion of the signal between leads 18 and wiper 24, which is applied to the A/D converter 26 and digital recorder 28, is also analog. A computer 30 is connected to the output of the A/D converter 26, is preferably IBM compatible, and is programmed in a manner described hereinafter.

Figure 3:
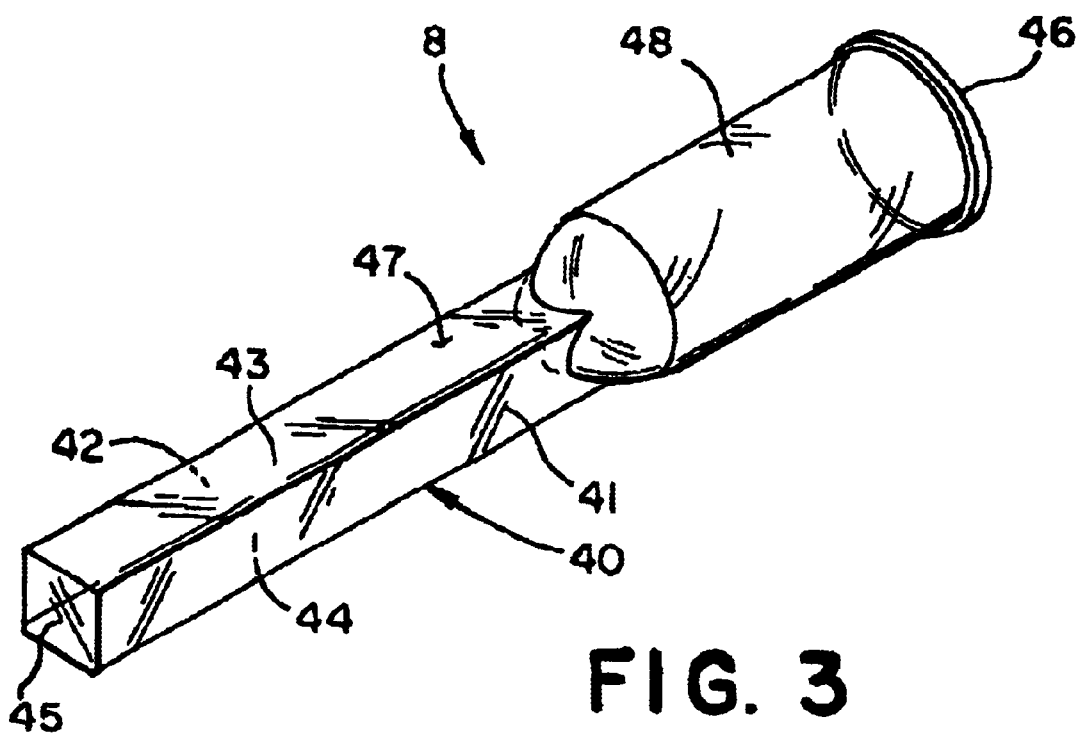
FIG. 3 is a parallel perspective view of a container constructed in accordance with the present invention.

The apparatus shown in FIG. 1 further has means for detecting movement across a range of a sample container 8. Preferably, as shown in FIG. 3, the sample container 8 is constructed in accordance with a preferred embodiment of the present invention and has a walled body portion 40 with a first pair of opposing walls 41, 42, a second pair of opposing walls 43, 44, and a bottom 45. A cover 46 is provided at the container end opposite the bottom 45 and seals the entrance to the container space 47. The body portion 40 of the container 8 is preferably formed by optical plastic or glass, and more preferably of the types known to be chemically inert to blood, its components and reagents used for the process and analysis to be carried out. The cover 46 prevents leakage of the container contents, while permitting the insertion of reagents and other chemicals through the cover. For example, a needle can be used to inject fluids into the container space 47.

The container 8, can be provided for use in carrying out particular procedures or analyses, such as, for example, coagulation studies. In a preferred embodiment according to the present invention, a thixotropic gel, such as a silicone compound, is provided in the container space 47 prior to the entry of blood or fluids. Calibration means for controlling the blood sampling amount to be taken up into the container 8 is provided. The calibration means in accordance with a preferred embodiment of the invention comprises a negative pressure applied in the container space 47, relative to the atmosphere, so that a vacuum is present in the space 47. The vacuum is controlled so that it pulls a predetermined quantity of blood into the container 8. The container top 46 is made from a material which maintains the vacuum and which also can be pierced by a needle such as those types of needles provided in needle holders which are used for venapuncture procedures. The blood is taken up through a needle inserted into and drawn into the container space 47.

The apparatus pictured in FIG. 1 further comprises detecting means for detecting along a predetermined path of travel, the path of travel being generally shown by the broken-line double arrow "a". The detecting means preferably comprises moving means for moving the optical detector such as the photovoltaic cell 10, and emitter light source 4 along a path of travel. The moving means in accordance with a preferred embodiment of the invention comprises a rack 50 which carries the cell 10 and the light source 4, and a stepper motor 51 mounted on the apparatus frame (not shown) and having a pinion 52 which is driven by the motor 51. The stepper motor 51 is controlled with suitable control means such as a lever, switch or the like, or an integrated circuit (not shown). The motor 51 drives the cell 10 and light source 4 along the optical walls 41, 42, 43, 44 of the container 8 in either direction as represented by double arrow "a". Preferably, the emitter light source comprises a light emitting diaode (LED) which is pared with the cell 10, preferably, a silicon cell, to form a LED-silicon cell fused pair which travels as a unit along the container 8. The operation of the motor 51 is coordinated by an operator, or with the use of software, for movement over the length of the sample tube body portion 40. The detector cell 10 is positioned adjacent an opposite wall of the sample container 8, such as that wall 41, and the emitter light source 4 positioned adjacent the opposite wall 42, so the light 6 emitted from the light source 4 passes through the container body 40. The light source 4 is preferably selected to produce light 6 which can be absorbed by one or more components which are to be measured.

Preferably, the light source 4 and photovoltaic cell 10 are positioned on a sleeve 70 which is attached to the rack 50. The sleeve 70 moves with the rack 50 along the vertical span of a pair of opposing sidewalls 41, 42, 43, 44 to scan the container contents.

Referring to FIG. 1, the container 8 is shown positioned in a holder 55 which is preferably mounted on the frame of the apparatus unit or housing (not shown) in which the electronic components are maintained. The container 8 preferably has a holding portion 48 which permits seating of the container 8 in the holder 55 of the apparatus.

The apparatus can be used to carry out coagulation studies. In accordance with a preferred embodiment of the present invention, the light source 4 comprises a light emitting diode (LED) emitting a wavelength of 660 nm, and the detector cell 10 comprises a silicon photovoltaic cell detector. A bar code reader 60 can also be provided to read bar code labels placed on the sample container 8. The bar code reader 60 can produce a signal which can be read by the computer 30 to associate a set of data with a particular sample container 8.

To carry out a coagulation study on blood plasma, the container 8 is prepared by adding a quantity of a blood preservative, such as 0.5 ml of a 3.2% sodium citrate anticoagulant, and a thixotropic gel, such as a silicone compound. The container 8 is stoppered with a cover 46 and a vacuum calibrated to aspirate via venapuncture a known volume of blood. Preferably, the amount of blood aspirated related to the amount of anticoagulant corresponding to a ratio of 1 part sodium citrate to 9 parts whole blood. The silicone used comprises a silicone having a specific gravity such that it floats on red blood cells and platelets, but is heavier than blood plasma. This permits the coagulation study to be carried out on blood plasma. Preferably, the silicone gel is friendly to PT's and PTT's, and has a specific gravity of between about 1.035 and 1.045 and it is most preferred that the specific gravity of the silicon gel be from about 1.035 and 1.039. The sample container 8 is centrifuged, preferably in excess of 4500 rpm and for about at least 5 minutes, to separate effectively and isolate the plasma from the formed elements of the blood, such as the red blood cells, platelets and white blood cells. The container 8 in FIG. 1 shows the separated blood, comprising a first lower level 61 containing red blood cells, white blood cells and most of the platelets, a second or central separating layer 62 comprised of a silicone compound, and a third level or upper layer 63 containing plasma and some platelets. The second layer 62 interfaces the first level 61 and third level 63. The specific gravity of whole human blood is generally within the range of about 1.048 to 1.066. The heavier red blood cell portion (red blood cells, white blood cells, platelets) of the whole blood has a specific gravity in the range of about 1.092 to 1.095, whereas the lighter serum or plasma portion has a specific gravity in the range of about 1.025 to 1.031. The coagulation study can now be carried out on the plasma sample which has been isolated in the top layer 63 of the sample container 8 without removing it or any of the components from the sample container 8.

Illustrative of the apparatus and method according to the present invention is a coagulation study which can be carried out therewith. A reagent, such as Thromboplastin-Calcium (Tp—Ca) is added to the plasma sample which is maintained at about 37° C. by any suitable temperature control device, such as a heated sleeve or compartment (not shown). The reagent addition is done by inserting a dispensing device, such as a needle through the cover 46 of the container 8, and injecting an appropriate amount of the reagent into the top layer 63. Preferably, venting means is provided to vent the container 8 when reagent is added to the container 8. The venting means while not shown can comprise a secondary needle extending through the container top 46 and into the container space 47. The reagent for example, may comprise thromboplastin, which is added in an amount equal to 2× the volume of the plasma or top layer 63. The injection dispenses the reagent and the force of the injection facilitates mixing of the reagent with the plasma. Air bubbles are minimized by the injection process so as not to interfere with the results. The injection is carried out without intrusion into the separating silicone layer 62 or the lower layer 61. The container 8 is heated to maintain a 37° C. temperature. This can be done by placing the container in a heating chamber (not shown). Preferably, however, while not shown, the holder 55 is configured with a thermostatically controllable warming element to maintain the temperature at 37° C.

Readings are taken of the optical activity of the components in the sample container 8. In this manner the volumes of the respective component layers can be determined. The stepper motor 51 rotates to move the detector 10 and light source 4 serially along the container 8, to pass the contents of the container 8. Since the red blood cell layer 61 and silicone layer 62 are substantially opaque, a smaller amount of light, if any, passes through the container 8, than passes through the plasma layer 63. However, the red blood cell layer 61 is optically distinguishable from silicone layer 62, and the apparatus detects the differences in the corresponding signal responses. The respective volumes of the component layers can be ascertained, as each layer 61, 62, 63 is optically distinguishable over each adjacent layer. The volume of red blood cells of the first layer 61 can be detected as the sleeve 70 or measuring module carrying the detector 10 and emitter 4 moves from the start of the container bottom 45 to the top of the first layer 61. The signal detected then changes as the silicone layer 62 is encountered, signifying the start of the silicone layer 62. The signal then undergoes a further change when the plasma layer 63 is reached, thus indicating the end of the silicone volume and the beginning of the plasma volume. The end of the plasma layer 63 is determined by a further signal change when the detector unit reaches the air space at the top of the plasma layer 63.

Since the volume of the silicone is a known quantity and the container 8 has equal cross-sectional areas over the container space 47 which holds the blood and silicone layers, the respective volumes of the plasma and red blood cell layers can be calculated, to give an approximation of the hematocrit and to ascertain that a full compliment of blood has been aspirated (i.e. that there has not been a "short draw").

Reaction kinematics can also be studied by observing changes in the optical density of the plasma layer. For example, an amount of reagent, such as Thromboplastin-Calcium (Tp—Ca), can be added to the container 8 through the cover 46 by penetration with a needle (not shown). The needle can be inserted manually or through a robotically controlled arm (not shown) which injects a controlled amount of Tp—Ca reagent into the container, and in particular into the plasma layer 63. The amount of reagent added corresponds to the amount of plasma volume detected by the pass of the detector 10 and emitter 4 along the sample layers. The computer 30 can compare the data for the known amount of silicone and operate a robotically controlled arm (not shown) to dispense a particular amount of reagent appropriate for the plasma sample volume determined. Preferably, the robotic arm has a plastic retractable sleeve which protects personnel from sharp needles. The detector cell 10 and emitter light source 4 are preferably positioned at the top of the plasma layer 63, so that when the reagent is added and the top layer 63 is thereby increased in volume, the detecting components (i.e. the light source 4 and detector cell 10) are positioned at approximately the center of the top layer 63.

Figure 2:
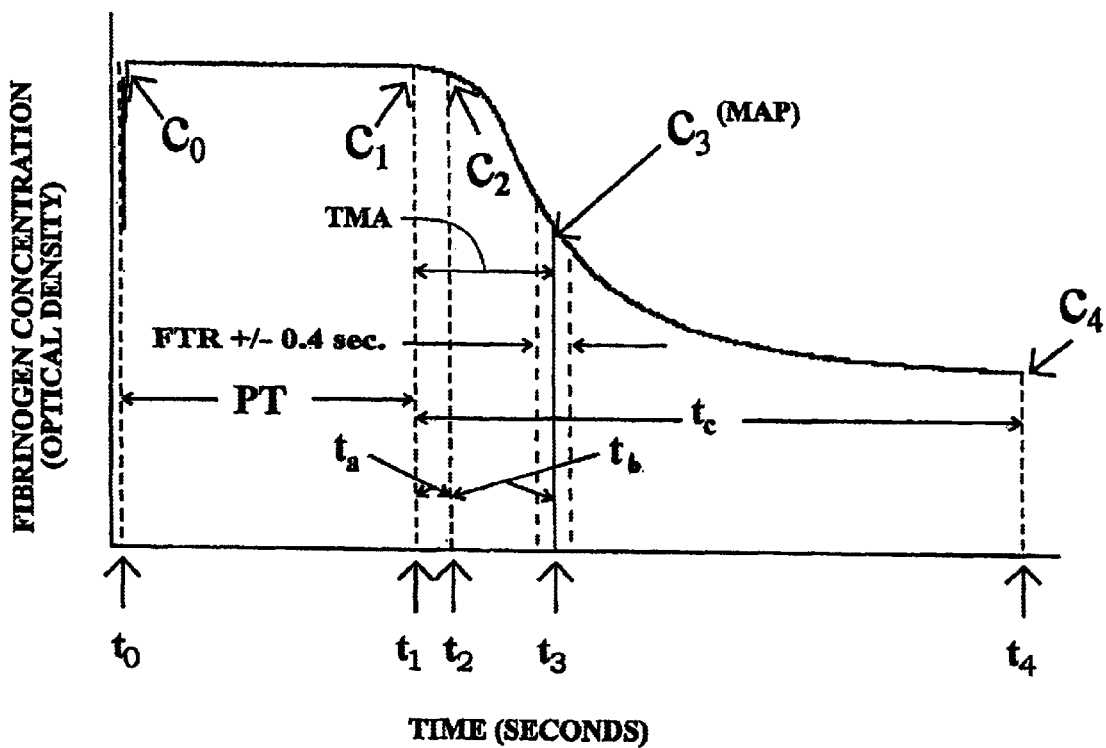
FIG. 2 is a plot of the various phases of the fibrinogen concentration occurring in a typical plasma clotting process.

With the detection elements, such as the cell 10 and emitter 4, positioned to read the plasma layer 63 containing the injected reagents, the reaction analysis of the extended prothrombin time curve can be followed. FIG. 2 shows a graph of a plot of the various phases of the fibrinogen concentration occurring in a typical plasma clotting process. The change in optical density of the plasma level occurs after reagents have been added. The optical density of the plasma layer is monitored, as optically clear fibrinogen converts to turbid fibrin.

When the prothrombin time and its subsequent measured entities, such as for example FBG, INR, CATF and MATF, are completed, the entire, intact, covered container 8 is removed from the detecting unit holder 55, either manually or with a robotic arm (not shown), and deposited into a waste receptacle. The present apparatus permits the receipt of a blood sample into the container 8 and contains the blood sample therein from the time of its withdrawal from a person throughout the entire testing process, including any warming steps, preprocessing steps, reaction steps, analyses steps and the disposal of the blood sample.

While described in connection with the coagulation study for determining PT from a plasma sample, it will be understood that other body fluid and blood chemistry studies, reactions, and analyses can be carried out with the apparatus and method of the present invention. The present invention is particularly useful for containing body fluids which require further processing and analysis.

The coagulation study of the type described above is used to ascertain the results shown in the graph plotted on FIG. 2. The description of the analysis makes reference to terms, and symbols thereof, having a general description as used herein, all to be further described and all of which are given in Table 1.

TABLE 1

| SYMBOL | TERM | GENERAL DESCRIPTION |
|---|---|---|
| PT | Prothrombin Time | A period of time calculated from the addition of thromboplastin-calcium to a point where the conversion of Fibrinogen to Fibrin begins. |
| TMA | Time to Maximum Acceleration | The time from PT to a point where the rate of conversion of Fibrinogen to Fibrin has reached maximum and begins to slow. |
| FTR | Fibrinogen Transformation Ratio | The amount of Fibrinogen converted during a time period from −½ TMA to +½ TMA. This is a percentage of the total Fibrinogen. |
| ATF | Anticoagulation Therapy Factor | The calculated value used to monitor the uses of an anticoagulant without a need for an International Sensitivity Index of a thromboplastin. |
| CATF | Corrected ATF | Change to the ATF calculation to give a better correlation of ATF vs. INR. |
| MATF | Modified ATF | A geometric modification making the value MATF equal to the value INR. |
| PR | Prothrombin Ratio | A value computed by dividing a sample PT by the geometric mean of at least 20 normal people (MNPT). |
| INR | International Normalized Ratio | A parameter which takes into account the various factors involved in anticoagulation therapy monitoring to provide a standardized system for monitoring oral anticoagulant therapy. |

For illustration, the present invention can be employed for accurate determination of prothrombin time (PT) and International Normalized Ratio (INR) from a human blood sample, for use during the monitoring of oral anticoagulant therapy, without the need for consideration of whether platelet rich plasma (PRP) or platelet poor plasma (PPP) is used. As is known in the art, blood clotting Factors I, II, V, VII, VIII, IX and X are associated with platelets (Bounameaux, 1957); and, among these, Factors II, VII, IX and X are less firmly attached, since they are readily removed from the platelets by washing (Betterle, Fabris et al, 1977). The role of these platelet-involved clotting factors in blood coagulation is not, however, defined. The present invention provides a method and apparatus for determining the PT, the INR and the diagnostic PTT of citrated human blood plasma where the platelet count is up to, and may exceed, $199 \times 10^9$ platelets/L. The known art has assumed that more than $10 \times 10^9$ platelets/L interfered with coagulation tests, since this is the maximum platelet level recommended for performing coagulation tests (NCCLS, 1998). A coagulation study was carried out, including an evaluation with specimens selected for study which were not in the normal range. This was done to accentuate the difference in clotting times between the PRP and PPP, so that any deficiencies would be exaggerated since the tests would be more sensitive. The selected specimens having known PTs of at least 15.7 sec., (whereas those of our laboratory's normal PT range is 11.8–13.5 sec.). These specimens would have had prolonged PTs because of warfarin depletion of the patient Factors II, VII, IX and X. PRP and PPP, throughout the study, were treated identically except for a mandatory second centrifugation and following pipetting of the PPP. PRP and PPP fluids should, therefore, be essentially identical with respect to coagulation capabilities, and differ only in their number of platelets.

Consideration of factors which could lead to potential problems were taken into account.

There could be disruption of the formed elements of the blood by centrifugation and vortexing for 1–2 minutes, but the blood did not show hemolysis (Gulati, Asselta et al, 1997). We observed platelet clumps, but no platelet fragmentation was seen with phase contrast microscopy of four sediment smears derived from plasmas centrifuged at 4500 rpm for 10 minutes. Group A underwent centrifugation and up to four hours of unstoppered air-exposure. $CO_2$ loss with pH increase would have occurred. The PPP in these samples was handled like the PRP except for a second centrifugation and the pipetting. Because of the buffering capacity of the thromboplastin reagent (Simplastin/PT-L), however, wide divergence in PRP and PPP coagulation test results would not be expected because of the differing plasma $PCO_2$ levels of the test specimens. Group B was centrifuged much less vigorously than group A so that it had considerably higher platelet counts and was exposed to air for less than 10 minutes, so its PRPs and PPPs would have close resemblance in their $P_{CO_2}$'S All plasma specimens were stored at 4°–6° C., for up to five hours; they were at room temperature for centrifugations and for up to four more hours. None of the patients was known to be on heparin. Valid PTs, INRs and PTTs should result under these conditions. Koepke, Rodgers et al (1975) and Brigden, Graydon et al (1997) state that PTs are stable for up to 24 hours after phlebotomy when the tubes are kept stoppered. Adcock, Kressen et al (1998) also indicate that PTs are stable up to 24 hours after phlebotomy, and PTTs are stable up to eight hours, except for patients on unfractionated heparin. The samples tested did not include patients on heparin. Since deterioration of Factors V and VIII would have been the same in PRPs and PPPs, even this does not present a problem.

It is noted that the PTs found in the pooled study specimens were shorter than would have been expected from the times of the specimens that were used to make up these pools. ANOVA comparison of the 223 original specimens ($\bar{x}=19.3$) with the 101 specimens that were created by pooling ($\bar{x}=17.0$), showed a significant difference (F=38.581, p<0.001). This is expected. Opitz and Zweig (1924) demonstrated that their recalcification clotting times in hemophiliac bloods shortened when platelets were stored for prolonged times (up to 27½ hours) in contact with their plasmas. This phenomenon did not occur in platelet-free plasma. These studies were confirmed by Brinkhous (1939), and both research groups attributed the changes to thromboplastin substances in the platelets. Since the thromboplastin release is slow, PTs are stable for 24 hours, PTTs are stable for eight hours (Adcock, Kressin et al 1998) and the platelet thromboplastin quantity is small compared to the amount of thromboplastin in the Simplastin/PT-L reagent, the paired plasma specimen PT shortening we saw is of no consequence to our experiments. A result of what an undefined consideration is in the effect of clotting factors is found in and on the platelets used for plasma clotting tests. Bounameaux (1957) described the elution of Factors II, VII, IX and X adsorbed to the platelets by repeat saline washes with centrifugations. He did not mention whether any of the adsorbed coagulation factors would separate with just a simple centrifugation, such as with our 10 minute, 4500 rpm spin. Betterle, Fabris et al (1977) confirmed the elution of II, VII, IX and X by using three washes and centrifugations with Tyrode's solution, but neither of these groups of authors used platelets depleted of these clotting factors in actual coagulation tests.

The effect of platelet numbers in Group A vs. Group B was compared by ANOVA. This series of analyses of variance showed no difference between the two sets of data on any of the dependent variables, so the data were combined for subsequent analyses. The t values for the combined analyses are shown in Table 2.

TABLE 2

|   | PT | INR | PTT |
|---|---|---|---|
| n | 100 | 100 | 97 |
| t | 0.325 | 0.373 | 0.586 |
| p | 0.745 | 0.709 | 0.559 |

Since the significance level ($\alpha$) was set at 0.01 to account for the large number of analyses, and the p values of the parameters (PT, INR, PTT) are much larger than 0.01, the PRP and PPP value differences are definitely not significant. Linear regression analyses for the combined 100 paired specimens are shown in Table 3.

TABLE 3

|   | PT | INR | PTT |
|---|---|---|---|
| n | 100 | 100 | 97 |
| Pearson's r | 0.9832 | 0.9829 | 0.9715 |
| Slope | 0.9421 | 0.9327 | 0.9538 |
| Intercept | 0.9341 | 0.1056 | 1.2058 |

These all show excellent correlation of the PRP-PPP specimen comparisons. The Bland-Altman plots demonstrated the interchangeability of the paired PRP and PPP samples. The 100 specimens were also separated into increments having PRP counts of $35-99 \times 10^9$/L, $100-199 \times 10^9$/L, and $200-575 \times 10^9$/L. The results show that there is no significant difference in any of the PT, INR or diagnostic PTT analyses for each of the sets of incremented paired specimens. This indicates that platelet counts of up to at least $200 \times 10^9$ platelets/L have no significant effect on any of these coagulation tests, and that results may be obtained at even much higher platelet count levels. This is seen in the anecdotal results illustrated with the paired specimens having the five highest platelet counts (Table 4).

TABLE 4

| Hi platelet count ($10^9$/L) | Lo platelet count ($10^9$/L) | PT_PRP | PT_PPP | INR_PRP | INR_PPP | PTT_PRP | PTT_PPP |
|---|---|---|---|---|---|---|---|
| 346 | 3 | 19.8 | 19.5 | 2.37 | 2.29 | 33.5 | 33 |
| 401 | 2 | 15 | 14.9 | 1.35 | 1.34 | 27.2 | 26.9 |
| 421 | 4 | 17.4 | 17.3 | 1.82 | 1.8 | 32.5 | 31.9 |
| 439 | 7 | 16.5 | 16.4 | 1.63 | 1.62 | 31.7 | 32 |
| 541 | 10 | 15.2 | 15.4 | 1.39 | 1.42 | N/S | N/S |
| 575 | 8 | N/S | N/S | N/S | N/S | 33.4 | 32.8 |

NS = Quantity of specimen not sufficient

Examination of the data presented in Table 4 shows that there are no statistically or clinically significant differences in PT, INR or PTT between PRP and PPP pairs that originated from the same plasmas.

It is known in the study of coagulation to hold to $<10\times10^9$ platelets/L as a prerequisite for coagulation studies. There have been large errors in platelet enumeration. According to Biggs and MacMillan (1948), the indirect platelet counting method of Dameshek (1932) had a coefficient of variation (C.V.) Of 41% while the direct method of Lempert had 23%. Brecher, Schneiderman et al (1953) used a direct phase microscopy method and had a C.V. of 22%. The modern, automated Coulter MAXM, in secondary mode, achieved a C.V. of 8% (personal observation). This all means that a platelet count of $10\times10^9$/L, with error, would not measure over $15\times10^9$/L. This does not approach $200\times10^9$/L, a level we have determined acceptable for PTs, INRs and diagnostic PTTs (patients not receiving heparin) obtained in accordance with the present invention. Partial explanation can be found in exploring the effect of $>10\times10^9$ platelets/L on tests for the Lupus Anticoagulant (LAC) and other phospholipid antibodies. Fantl and Ward (1958) demonstrated that a phospholipid (PL), present in platelets, became active in their rate of thrombin formation test, only when the platelets had been previously frozen and thawed. Unfrozen platelets were inactive. For heparin monitoring, platelet counts of less than 10,000 are required to carry out a study, since if Platelet Factor 4 is liberated it neutralizes the heparin and alters the results. Disrupting the platelet structure by freezing-thawing apparently liberated the PL component. This PL was free to neutralize the LAC antibodies, and, thereby, interfere with, or even invalidate, the LAC tests such as the Platelet Neutralizing Procedure (PNP) (Triplett, Brandt et al 1983). PL release from platelets decreases clotting times, but significant amounts cannot have been released in our experiments or PTs would not have been reported stable for 24 hours and PTTs for eight hours. (Adcock, Kressin et al 1998). Since LAC test plasmas are frequently frozen for later batch processing or for shipment to a reference laboratory for testing, PL liberation by freezing the platelets accounts for the stringent requirements for platelet counts in the LAC procedures.

The International Normalized Ratio (INR) is previously discussed in already incorporated reference technical articles entitled "PTs, PRs, ISIs and INRs: A Primer on Prothrombin Time Reporting Part I and II respectively," published November, 1993 and December, 1993 issues of *Clinical Hemostasis Review*. The illustrative example of an analysis which is carried out employing the present invention relies upon the prothrombin time (PT) and a fibrinogen transformation rate (FTR), that is, the thrombin activity in which fibrinogen (FBG) is converted to fibrin to cause clotting in blood plasma. The analysis also relies upon a particular understanding of the enzymatic clotting steps occurring during a prothrombin time (PT) of plasma having proteins including factors II, IIa, V, VII, and X.

More particularly, during the clotting steps used to determine the clotting process of a plasma specimen of a patient under observation, a thromboplastin (Tp) activates factor VII which, activates factor X, which, in turn, under catalytic action of factor V, activates factor II (sometimes referred to as prothrombin) to cause factor IIa (sometimes referred to as thrombin) that converts fibrinogen (FBG) to fibrin with resultant turbidity activity which is measured, in a manner as to be described hereinafter, when the reaction is undergoing simulated zero-order kinetics.

From the above, it should be noted that the thromboplastin (Tp) does not take part in the reaction where factor IIa (thrombin) converts fibrinogen (FBG) to fibrin which is deterministic of the clotting of the plasma of the patient under consideration. The thromboplastin (Tp) only acts to activate factor VII to start the whole cascade rolling. Note also that differing thromboplastins (Tps) have differing rates of effect on factor VII, so the rates of enzyme factor reactions up to II–IIa (the PT) will vary.

Therefore, the prothrombin times (PTs) vary with the different thromboplastins (Tps) which may have been a factor that mislead authorities to the need of taking into account the International Normalized Ratio (INR) and the International Sensitivity Index (ISI) to compensate for the use of different types of thromboplastins (Tps) during the monitoring of oral anticoagulant therapy. It is further noted, that thromboplastins (Tps) have nothing to do with factor IIa converting fibrinogen (FBG) to fibrin, so it does not matter which thromboplastin is used when the fibrinogen transformation is a primary factor.

The thromboplastin (Tp) is needed therefore only to start the reactions that give factor IIa. Once the factor IIa is obtained, fibrinogen (FBG) to fibrin conversion goes on its own independent of the thromboplastin (Tp) used. Accordingly, for example in measuring the anticoagulant therapy factor (ATF), one needs only take into account the determination of the fibrinogen transformation rate (FTR), the prothrombin time (PT) and the maximum acceleration point (MAP), all of which may be typically ascertained by the use of fibrinogen solutions. This coagulation study is discussed further in U.S. Pat. No. 5,502,651.

The present method and apparatus has use, for example, in coagulation studies where fibrinogen (FBG) standard solutions and a control solution are employed, wherein the fibrinogen standard solutions act as dormant references to which solutions analyzed with the present invention are compared, whereas the control solution acts as a reagent that is used to control a reaction. The fibrinogen standards include both high and low solutions, whereas the control solution is particularly used to control clotting times and fibrinogens of blood samples.

A fibrinogen (FBG) solution of 10 g/l may be prepared from a cryoprecipitate. The cryoprecipitate may be prepared by freezing plasma, letting the plasma thaw in a refrigerator and then, as known in the art, expressing off the plasma so as to leave behind the residue cryoprecipitate. The gathered cryoprecipitate should contain a substantial amount of both desired fibrinogen (FBG) and factor VIII (antihemophilic globulin), along with other elements that are not of particular concern to the present invention. The 10 g/l fibrinogen (FBG) solution, after further treatment, serves as the source for the high fibrinogen (FBG) standard. A 0.5 g/l fibrinogen (FBG) solution may then be prepared by a 1:20 (10 g/l/20= 0.5 g/l) dilution of some of the gathered cryoprecipitate to which may be added an Owren's Veronal Buffer (pH 7.35) (known in the art) or normal saline solution and which, after further treatment, may serve as a source of the low fibrinogen (FBG) standard.

The fibrinogen standard can be created by adding fibrinogen to normal plasma in an empty container. Preferably, the fibrinogen standard is formed from a 1:1 fibrinogen to normal plasma solution. For example, 0.5 ml of fibrinogen and 0.5 ml of plasma can be added together in an empty container. The volume of the container can then be ascertained by a scan with the apparatus 10. Thromboplastin calcium is then added to the fibrinogen standard. Preferably, 2× the amount by volume of thromboplastin is added into the container 8 per volume amount of fibrinogen standard which is present in the container 8. The reaction is watched with the apparatus 10.

Then, 1 ml of each of the high (10 g/l) and low (0.5 g/l) sources of the fibrinogen standards may be added to 1 ml of normal human plasma (so the cryoprecipitate plasma solution can clot), and this addition respectively may yield 6.38 g/l and 1.5 g/l high and low fibrinogen (FBG) standards, used for analyzing samples of citrated blood under test, especially those samples being monitored during oral anticoagulant therapy which is of prime importance to the present invention. The addition of a fibrinogen standard preferably is added to the plasma layer 63 based on the volume of the plasma 63 ascertained by a potentiophotometric scan of the contents of the container 8 using the apparatus shown in FIG. 1.

As is known, the addition of the reagent Thromboplastin ● C serves as a coagulant to cause clotting to occur within a sample of citrated blood under test which may be contained in a the container 8. As clotting occurs, the A/D converter 26 of FIG. 1 will count and produce a digital value of voltage at a predetermined period, such as once every 0.05 or 0.01 seconds. As more fully described in the previously incorporated by reference U.S. Pat. No. 5,197,017 ('017), these voltage values are stored and then printed by the recorder as an array of numbers, the printing being from left to right and line by line, top to bottom. There are typically one hundred numbers in the five groups representing voltage values every second and hence, one line represents one-fifth of a second in time (20×0.01 seconds). Individual numbers in the same column are twenty sequential numbers apart. Hence, the time difference between two adjacent numbers in a column is one-fifth of a second. The significance of these recorded values may be more readily appreciated after a general review of the operating principles illustrated in FIG. 2 having a Y axis identified as Fibrinogen Concentration (Optical Density) and a X axis identified in time (seconds).

FIG. 1 shows a sample container 8 provided with a silicone gel disposed therein which has been spun to separate blood components into a red first layer 61 containing red blood cells, white blood cells, and platelets; a silicone layer 62 and a plasma layer (with some platelets) 63.

FIG. 2 illustrates the data point locations of a clotting curve related to a coagulation study which can be carried out with the present invention. In general, FIG. 2 illustrates a "clot slope" method that may be used in a blood coagulation study carried out by the present invention for determining an anticoagulant therapy factor (ATF). This study is more fully discussed in the previously incorporated by reference U.S. Pat. No. 5,502,651 which measures the concentration of the fibrinogen (FBG) in the plasma that contributes to the clotting of the plasma and uses the potentiophotometer apparatus of FIG. 1 to provide an output voltage signal that is directly indicative of the fibrinogen (FBG) concentration in the plasma layer 63 of the sample under test contained in the container 8. The quantities given along the Y-axis of FIG. 2 are values (+and−) that may be displayed by the digital recorder 28. The "clot slope" method comprises detection of the rate or the slope of the curve associated with the formation of fibrin from fibrinogen. The "clot slope" method takes into account the prothrombin time (PT) (previously mentioned as one of the factors for determining the anticoagulant therapy) which is typically defined as the time duration between the injection of a reagent, such as thromboplastin and calcium ion, through the cover 46 and into the plasma layer 63, and the corresponding instant of time when the clotting process begins.

As seen in FIG. 2, at time $t_0$, corresponding to a concentration $c_0$, the thromboplastin/calcium ion reagent is introduced into the blood plasma which causes a disturbance to the composition of the plasma layer 63 of the spun blood sample which, in turn, causes the optical density of the plasma layer 63 to increase momentarily. After the injection of the reagent (the time of which is known, as to be described, by the computer 30), the digital quantity of the recorder 28 of FIG. 1 rapidly increases and then levels off in a relatively smooth manner and then continues along until the quantity $c_1$ is reached at a time $t_1$. The time which elapses between the injection of thromboplastin at $t_0$ and the instant time $t_1$ of the quantity $c_1$ is the prothrombin time (PT) and is indicated in FIG. 2 by the symbol PT. The prothrombin time (PT) is of primary importance in a coagulation study, such as the one described herein, because it is one of the three parameters (the other are the fibrinogen transformation rate (FTR) and the maximum acceleration point (MAP) having associated with it a time to maximum acceleration (TMA)) that determines the anticoagulant therapy factor (ATF).

The optical density of the quantity cl directly corresponds to a specified minimum amount of fibrinogen (FBG) that must be present for a measuring system, such as the circuit arrangement of FIG. 1, to detect in the plasma layer 63 that a clot is being formed. Further., all the quantities shown in FIG. 2 are of optical densities that are directly correlatable to fibrinogen concentration values. The critical quantity $c_1$, may vary from one clot detection system to another, but for the potentiophotometer system of FIG. 1, this minimum is defined by units of mass having a value of about 0.05 grams/liter (g/l).

The detection of this first predetermined quantity $c_1$ is shown in FIG. 2 to occur at an instant time $t_1$ which is the start of the clotting process being monitored with the apparatus of FIG. 1 for determining the anticoagulant therapy factor (ATF). The time $t_1$ is the beginning point of the fibrinogen formation, that is, it is the point that corresponds to the beginning of the acceleration of the fibrinogen conversion that lasts for a predetermined time, preferably about 1.5 seconds. This $t_1$ point is determined by a real time analysis of the optical density data accumulated during testing. The time duration of at least 1.5 seconds allows a sufficient amount of delay time to eliminate any false responses due to noises created by initial mixing of the reagent into the sample or bubbles within the sample under test. This 1.5 second duration helps determine the beginning point ($t_1$) of the fibrinogen conversion in spite of any bubbles or artifacts that might be present for short durations. These noise producers might otherwise be erroneously interpreted as early clots and might lead to a correspondingly false response by the instrument performing the measuring. Accordingly, the noise time may be greater or less than the 1.5 seconds, as needed, and can be adjusted by programming the computer 30.

The acceleration of the fibrinogen conversion that occurs within the 1.5 second duration, is shown in FIG. 2 as a first time period $t_a$ ($t_1$ to $t_2$). This first time period $t_a$ is defined by the first quantity $c_1$ and a second $c_2$ occurring at a time $t_2$, wherein $c_2$ has a value equal to at least $c_1$. The acceleration of the fibrinogen conversion continues until a time $t_3$, having a corresponding quantity $C_3$. The time $t_3$, as well as the quantity $C_3$, is of primary importance because it is the point of maximum acceleration of the fibrinogen (FBG) to fibrin conversion and is also the point where deceleration of fibrinogen (FBG) to fibrin conversion begins. Further, the elapsed time from $t_1$ to $t_3$ is a time to maximum acceleration (TMA), shown in FIG. 2, which serves as a multiplier (TMA)/100 to be described. The third quantity ($C_3$) and the time $t_3$ define a maximum acceleration point (MAP) and are shown in FIG. 2 as having predetermined ranges starting prior to maximum acceleration point (MAP) and ending after the maximum acceleration point (MAP), with the difference covered by the overall range defining the fibrinogen transformation rate (FTR), which is also shown in FIG. 2 and has a typical band of +/−0.5 seconds. Fibrin formation, after a short lag phase before the MAP, occurs for a period of time, in a linear manner. Fibrinogen (FBG) is in excess during this lag phase, and fibrin formation appears linear up to the MAP. The FBG formed during an interval from +/− (TMA÷2) seconds of the MAP is given as a percentage of the total clottable FBG. This is the fibrinogen transformation rate (FTR). The fibrinogen transformation rate (FTR) is of primary importance in the coagulation study exemplified herein because it is one of the three parameters that determine the anticoagulant therapy factor (ATF) of the present invention with the other two being the prothrombin time (PT) and the maximum acceleration point (MAP). The predetermined range may be from about 0.1 seconds to about 5.0 seconds on each side of the maximum acceleration point (MAP) shown in FIG. 2 so that the fibrinogen transformation rate (FTR) may cover an overall difference from about 0.2 seconds to about 10.0 seconds.

The times $t_3$ and $t_2$ define a second time period $T_b$ which has a typical value of 1.5 seconds. The deceleration of fibrinogen (FBG) to fibrin conversion continues until a quantity $c_4$ is reached at a time $t_4$. The time $t_4$ is the point where the deceleration of the fibrinogen (FBG) to fibrin conversion corresponds to a value which is less than the required amount of fibrinogen (FBG) that was present in order to start the fibrinogen (FBG) to fibrin conversion process. Thus, because the desired fibrinogen (FBG) to fibrin conversion is no longer in existence, the time $t_4$ represents the ending point of the fibrinogen (FBG) to fibrin conversion in accordance with the coagulation study exemplified herein. The fibrinogen (FBG) to fibrin conversion has a starting point of $t_1$ and an ending point of $t_4$. These times $t_1$ and $t_4$ define a third period $T_c$.

The significance of the points ($t_1$, and $t_4$) are not the times at which they occur, but rather the difference in the optical density of the quantities $c_1$ and $c_4$ occurring at the times $t_1$ and $t_4$. This difference is defined herein as the delta optical density of the "clot slope" method and is of importance to determining the anticoagulant therapy factor (ATF). The "clot slope" method that gathers typical data as shown in FIG. 2 has four critical parameters. The first is that the initial delta optical density of substance being analyzed should be greater than about 0.05 g/l in order for the circuit arrangement of FIG. 1 to operate effectively. Second, the acceleration (fibrinogen ((FBG)) to fibrin conversion associated with $T_a$) should be increasing for a minimum period of about 1.5 seconds so as to overcome any false reactions created by bubbles. Third, the total delta optical density (defined by the difference in quantities $c_1$ and $c_4$) should be at least three (3) times the instrument value in order to perform a valid test, i.e., (3)*(0.05 g/l)=0.15 g/l. Fourth, the fibrinogen (FBG) to fibrin conversion is defined, in part, by the point ($t_4$) where the deceleration of conversion becomes less than the instrument value of about 0.05 g/l that is used to detect the clot point ($t_1$). As with most clot detection systems, a specific amount of fibrinogen needs to be present in order to detect a clot forming. Adhering to the four given critical parameters is an example of how the present apparatus can be used to carry out a coagulation study to determine a specific quantity of fibrinogen. In order for that specific amount of fibrinogen to be determined, it is first necessary to detect a clot point ($t_1$). After that clot point ($t_1$) is detected, it logically follows that when the fibrinogen conversion becomes less than the specific amount (about 0.05 g/l for the circuit arrangement of FIG. 1), the end point ($t_4$) of the fibrinogen conversion has been reached.

The gathering, storing, and manipulation of the data generally illustrated in FIG. 2, is primarily accomplished by computer 30 of FIG. 1 that receives digital voltage values converted, by the A/D converter 26, from analog voltage quantities of the photocell 10 detection means.

The preferred IBM-compatible computer 30 of FIG. 1 stores and manipulates these digital values corresponding to related data of FIG. 2 and is preferably programmed as follows:

(a) with citrated blood, such as described above in the container 8, the computer 30, as well as the recorder 28, sequentially records voltage values for a few seconds before injection of thromboplastin. As previously discussed, thromboplastin is one of the factors in the human body that causes blood to clot. Prothrombin is another. Fibrinogen is yet another. Before injection of the thromboplastin, the output from the A/D converter 26 is relatively constant. When thromboplastin is injected into the plasma layer 63 in the container 8, a significant and abrupt change occurs in the recorded voltage values of both the computer 30 and the recorder 28. This abrupt change is recognized by both the recorder 28 and, more importantly, by the computer 30 which uses such recognition to establish to already discussed with reference to FIG. 2. The computer 30 may be programmed so as to correlate the digital quantities of the A/D converter 26 to the analog output of the detector means photocell 10 which, in turn, is directly correlatable to the fibrinogen (FBG) concentration g/l of the sample of blood discussed with reference to FIG. 2;

2), the computer 30 may be programmed to look for a digital quantity representative of the previously discussed critical quantity $c_1$, and when such occurs, record its instant time $t_1$. The time span between $t_0$ and $t_1$ is the prothrombin time (PT) of particular importance to the coagulation study exemplified herein and has a normal duration of about 12 seconds, but may be greater than 30 seconds;

(c) following the detection of the critical quantity $c_1$, the computer 30 may be programmed to detect for the acceleration of fibrinogen (FBG) to fibrin conversion within the defined time period $T_a$, having a typical duration of 1.5 seconds. The parameters of this time period $T_a$ are its beginning which is defined by the occurrence ($t_1$) of the first predetermined quantity $c_1$ and its end which is defined by the second predetermined quantity $c_2$ occurring at time $t_2$. The first predetermined time period $T_a$ has a typical range of about 12 to about 30 seconds as measured from $t_0$. The computer 30 is also programmed to detect the maximum acceleration quantity $c_3$ and its time of occurrence $t_3$ (having a typical value of 1.5 seconds after $t_2$). These two times $t_2$ and $t_3$ define the time duration $T_b$. Furthermore, the computer detects the quantity $c_4$ occurring at time $t_4$ so as to define the time duration $T_c$. The time period $t_a$ may exceed but may not be less than the typical 1.5 second duration. The duration of the time between the occurrence ($t_1$) of the quantity $c_1$, and the occurrence ($t_2$) of the quantity $c_2$ is not fixed. It is only important that the rate of fibrin formation increase for at least 1.5 second following the occurrence of ($t_1$);

(d) following the detection of the maximum acceleration quantity $C_3$ and the time $t_3$ both of which define the maximum acceleration point (MAP), the computer 30 is programmed to determine the fibrinogen transformation rate (FTR) covering a predetermined range starting prior to the maximum acceleration point (MAP) and ending after the maximum acceleration point (MAP). The elapsed time from $t_1$ to $t_3$ is the time to maximum acceleration (TMA) shown in FIG. 2 and is a multiplier factor (TMA/100). The fibrinogen transformation rate (FTR) has an upwardly rising (increasing quantities) slope prior to the maximum acceleration point (MAP) and, conversely, has a downwardly falling (decreasing quantities) slope after the maximum acceleration point (MAP). The computer 30 is programmed to allow for a predetermined range defining the fibrinogen transformation rate (FTR) which may be from about 0.1 seconds up to 5.0 seconds on each side of the maximum acceleration point (MAP) so that the fibrinogen transformation rate (FTR) may cover an overall difference from about 0.2 seconds to about 10.0 seconds;

(e) following the detection of the acceleration of fibrinogen conversion, the computer 30 is programmed to detect for a deceleration of the fibrinogen conversion, wherein the fibrinogen concentration decreases from its third predetermined quantity $c_3$ to a fourth predetermined quantity $c_4$ having a value which is about equal but less than the first quantity $c_1$. The time duration from the instant time of the detection of the first quantity $c_1$ to the instant time of the detection of the fourth quantity $c_4$, defines the third period $T_c$;

f) the computer 30 manipulates the collected data of(a); b); (c); (d) and (e) above, to determine the prothrombin time (PT) based on the principle that if a required amount (e.g., 0.05 g/l) of fibrinogen concentration $c_1$ is first necessary to detect a clot point ($t_1$); then when the fibrinogen concentration ($c_4$) becomes less than the required amount $c_1$, which occurs at time ($t_4$), the fibrinogen end point has been reached. More particularly, the required fibrinogen concentration $c_1$ is the starting point of fibrinogen conversion of the clotting process and the less than required fibrinogen concentration $c_4$ is the end point of the fibrinogen conversion of the clotting process. Thus, the duration of the fibrinogen conversion of the clotting process of the present invention is defined by the time period between $t_1$ and $t_4$ and is generally indicated in FIG. 2 as $T_c$; and (g) the computer 30 now has the information needed todetermine the INR, which typically is expressed as:

$$INR = \left[\frac{\text{Patient's } PT}{\text{Geometric Mean of } PT \text{ Normal Range}}\right]^{ISI} \quad (2)$$

In carrying out coagulation studies, in one analysis the INR is replaced by the anticoagulant therapy factor (ATF), in accordance with the determination disclosed in U.S. Pat. No. 5,981,285. More particularly, the computer 30 has knowledge of the fibrinogen transformation rate (FTR) and the prothrombin time (PT) and a simple division routine, run in the computer 30, the product which, when multiplied by the time to maximum acceleration (TMA), yields the anticoagulant therapy factor (ATF) of the present invention having the relationship given by the below expression (2):

$$ATF = PT/FTR*(TMA/100) \quad (3)$$

It should now be appreciated that the present invention provides a contained and automatic method for obtaining an anticoagulant therapy factor (ATF) without encountering the complications involved with obtaining the prior art quantities International Normalized Ratio (INR) and International Sensitivity Index (ISI) having a relationship defined by the below expression (3) as well as the quantity $$\left[\frac{\text{Patient's } PT}{\text{Geometric Mean of } PT \text{ Normal Range}}\right]$$

referred to as the prothrombin ration (PR) all discussed in the "Background" section:

$$INR = \left[\frac{\text{Patient's } PT}{\text{Geometric Mean of } PT \text{ Normal Range}}\right]^{ISI} \quad (4)$$

In one type of analysis, the anticoagulant therapy factor (ATF) is a replacement for the International Normalized Ratio (INR); however, the existing medical literature, instrumentation, and methodologies are closely linked to the International Normalized Ratio (INR) and, therefore, as disclosed in U.S. Pat. No. 5,981,285, the ATF is correlated, by comparative testing, to INR quantities to each other even with the understanding that the INR determination may have an error of about thirteen (13) % which needs to be taken into account to explain certain inconsistencies.

Although the hereinbefore description of anticoagulant therapy factor (ATF) does correlate well with the International Normalized Ratio (INR) when most of the patients being sampled were using a particular therapy, such as the anticoagulant Coumadin (previously discussed), it does suffer discrepancies when the ATF and INR quantities are compared for individual patients. These discrepancies are resolved when the anticoagulant therapy factor is statistically corrected, hereinafter referred to as corrected anticoagulant therapy factor (CATF), by the below expression (4):

$$CATF = PT*PR/FTR*(TMA/100) \quad (5)$$

where the prothrombin ratio, PR, as used herein, =PT/MNPT, and the mean normal prothrombin time (MNPT), as used herein, is the geometric mean of the prothrombin time (PT) from at least 20 normal patients. The usage of the prothrombin ratio, PR, quantity in expression (4) more evenly spreads out the values of the prothrombin time, PT, quantity so as to yield a more sensitive CATF quantity of expression (4) as compared to the sensitivity of the ATF quantity of expression (2).

In general, it is desired to "correct" the ATF of expression (2) to be that of expression (4), so that the corrected anticoagulant therapy factor (CATF) corresponds as well as possible to the INR numerically.

In accordance with the calculations disclosed in U.S. Pat. No. 5,981,285, the computer 30 may be used to manipulate and derive the quantities of expression (4) utilizing known programming routines and techniques. The data collected by a computer 30 used to manipulate and derive the anticoagulant therapy factor (ATF) of expression (2) may be used and becomes the same data that is used to manipulate and derive the corrected anticoagulant therapy factor (CATF) of expression (4). The data can be collected for the blood sample and the calculations carried out without having to remove blood from the sample container 8. Similarly, one skilled in the art, using known mathematical techniques may derive the prothrombin ratio (PR) and the mean normal prothrombin time (MNPT) of expression (4) which, in turn, are used to determine the corrected anticoagulant therapy (CATF) of expression (4). The accuracy of these quantities is dependent, in part, on the number of specimens used, that is, the number of stable patients; wherein for the practice of this embodiment of the present invention, as more particularly discussed in U.S. Pat. No. 5,981,285, with reference to a calibration procedure, a number of at least twenty (20) of stable patients is preferably used and which is in agreement with that used in the art to establish a population sampling standard, such as disclosed in the previously incorporated by reference technical article of L. Poller et al.

While the invention has been described with reference to specific embodiments, the description is illustrative and is not to be construed as limiting the scope of the invention. For example, although described in connection with body fluids of a human, the present invention has applicability to veterinary procedures, as well, where fluids are to be measured or analyzed. Various modifications and changes may occur to those skilled in the art without departing from the spirit and scope of the invention described herein and as defined by the appended claims.

What we claim is:

1. A method of conducting coagulation studies and other chemistry procedures on a blood or fluid sample, comprising the steps of:
   a. providing a closed sample container having optically clear sides and a covered opening, with the container having therein a thixotropic substance, an anticoagulant and a vacuum pressure corresponding to a predetermined amount of a volume of a fluid to be aspirated into the sample container;
   b. aspirating a sample of a body fluid into the container by puncturing the covered opening;
   c. centrifuging the container with the fluid sample of step (b);
   d. placing the container with the fluid sample centrifuged in step (c) into a potentiophotometer having at least one emitting light source and at least one detecting cell;
   e. scanning the sample in the container with at least one emitting light source positioned on one side of the container and detecting with at least one detector cell positioned on the opposite side of the container to determine the absorption of the fluid sample or one or more components of the fluid sample.

2. The method of claim 1, wherein the step of providing a closed sample container having therein a thixotropic substance, includes providing a silicone compound as the thixotropic substance.

3. The method of claim 1, wherein the step of scanning the fluid sample includes moving the detector cell and the emitting light source relative to the container, simultaneously across at least a portion of the container.

4. The method of claim 1, further comprising the step of storing the data obtained from the scanning of the fluid sample.

5. The method of claim 3, further comprising the steps of storing the data obtained from the scanning of the fluid sample and calculating from the data obtained the volume of one or more components of the fluid sample.

6. The method of claim 1, further comprising the step of adding to the container containing a sample of a body fluid therein, at least one reagent.

7. The method of claim 6, wherein said at least one reagent comprises thromboplastin.

8. The method of claim 3, further comprising the step of obtaining output data from the scanning of the fluid sample and comparing differences between output data obtained at various points along the container to ascertain the volume of the container and the volume of one or more component layers of the container.

9. The method of claim 1, wherein the method further includes the step of determining the value of one or more of the prothrombin times, International Normalized Ratios and partial thromboplastin times for the fluid sample when the fluid sample is a blood sample, wherein the data used for determining the value of one or more of the prothrombin times, International Normalized Ratios and partial thromboplastin times for the fluid sample is obtained with the fluid sample in the container into which it was originally aspirated from a patient in step (b).

10. The method of claim 1, further comprising the step of disposing of the fluid sample mixture by disposing of the container with the fluid sample contained therein.

11. The method of claim 1, wherein step (d) includes maintaining the fluid sample at a temperature of about 37° C.

12. The method of claim 1, wherein the step of centrifuging the container with the fluid sample comprises the step of separating the fluid sample into one or more layers including at least an upper layer which contains the components of the fluid sample to be studied, and wherein the method further comprises the step of adding to the upper layer a calculated volume of reagent appropriate to the test being carried out.

13. The method of claim 12, wherein the method is carried out using a fluid sample which comprises human blood, and wherein the step of adding a reagent comprises adding an anticoagulant as a reagent.

14. The method of claim 12, wherein the method is carried out using a fluid sample which comprises human blood, and wherein the step of adding a reagent comprises adding thromboplastin-calcium as a reagent.

15. The method of claim 14, wherein the upper layer contains plasma, and wherein the thromboplastin-calcium is added in an amount by volume equal to twice the volume of the upper layer.

16. The method of claim 15, wherein the anticoagulant comprises sodium citrate, and wherein the volume ratio of human blood to the anticoagulant is 9:1.

17. The method of claim 10, wherein the sample of human blood in step (a) has a prothrombin time greater than 8.0 seconds.

18. The method of claim 1, wherein the centrifuging in step (c) is carried out at about 4500 rpm (2183 g) for about five minutes.

19. The method of claim 13, wherein the anticoagulant therapy factor is prothrombin time.

20. The method of claim 13, wherein the anticoagulant therapy factor is International Normalized Ratios.

21. The method of claim 1, wherein the steps of aspirating a sample of body fluid is carried out by drawing body fluid through a needle.

22. A method of conducting coagulation studies and other chemistry procedures on a blood or fluid sample, comprising the steps of:
(a) providing a closed sample container having optically clear sides and a covered opening covered by a pierceable cover, with the container having therein silicone, an anticoagulant and a vacuum pressure corresponding to a predetermined amount of a volume of a fluid to be aspirated into the sample container;
(b) introducing into the container through said pierceable cover a sample of a body fluid by drawing from a patient's body a body fluid and admitting said body fluid to the container through a puncture in the covered opening;
(c) injecting a reagent into the container through said pierceable cover;
(d) analyzing the sample contents at one or more times during the method.

23. A method of conducting coagulation studies and other chemistry procedures on a blood or fluid sample, comprising the steps of:
(a) providing a closed sample container having optically clear sides and a covered opening covered by a pierceable cover, with the container having therein silicone, an anticoagulant and a vacuum pressure corresponding to a predetermined amount of a volume of a fluid to be drawn into the sample container;
(b) drawing from a patient's body a sample of a body fluid into the closed sample container;
(c) placing the container with a fluid sample into a potentiophotometer having at least one emitting light source and at least one detecting cell;
(d) scanning the sample while it is in the container using the potentiophotometer to measure properties of the sample.

24. The method of claim 23, further comprising the step of adding a computer determined amount of reagent specific for the coagulation study being carried out.

25. The method of claim 24, wherein the step of adding a computer determined amount of reagent comprises adding thromboplastin.

26. The method of claim 23, further comprising the step of centrifuging the container with the sample of a body fluid therein after the sample has been drawn into the container and prior to placing the container with a fluid sample into a potentiophotometer, to separate substantially the plasma from the red blood cell, white blood cell, and platelet components of blood.

27. The method of claim 26, further comprising adding a reagent to the plasma layer.

28. The method of claim 27, wherein the step of adding a reagent to the plasma layer, comprising adding thromboplastin.

29. The method of claim 24, further comprising the step of carrying out a reaction with the sample in the container.

30. The method of claim 23, wherein the step of drawing a sample of a body fluid into the closed sample container comprises aspirating the sample from a body.

31. A method of conducting coagulation studies and other chemistry procedures on a blood or fluid sample, comprising the steps of:
a. providing a closed sample container having optically clear sides and a covered opening, with the container having therein a thixotropic substance, an anticoagulant and a vacuum pressure corresponding to a predetermined amount of a volume of a fluid to be aspirated into the sample container;
b. aspirating a sample of a body fluid into the container by puncturing the covered opening;
c. centrifuging the container with the fluid sample of step (b);
d. placing the container with the fluid sample centrifuged in step (c) into a potentiophotometer having at least one emitting light source and at least one detecting cell;
e. scanning the sample in the container with at least one emitting light source positioned on one side of the container and detecting with at least one detector cell positioned on the opposite side of the container to determine the absorption of the fluid sample or one or more components of the fluid sample;
f. analyzing the sample by reacting the sample with one or more reagents while the sample remains in the container.

32. The method of claim 31, including obtaining a result from the reaction of the sample with one or more reagents.

33. A method of conducting coagulation studies and other chemistry procedures on a blood or fluid sample, comprising the steps of:
a. providing a closed sample container having optically clear sides and a covered opening, with the container having therein a thixotropic substance, an anticoagulant and a vacuum pressure corresponding to a predetermined amount of a volume of a fluid to be aspirated into the sample container;
b. aspirating a sample of a body fluid into the container by puncturing the covered opening;
c. centrifuging the container with the fluid sample of step (b);
d. placing the container with the fluid sample centrifuged in step (c) into a potentiophotometer having at least one emitting light source and at least one detecting cell;
e. scanning the sample in the container with at least one emitting light source positioned on one side of the container and detecting with at least one detector cell positioned on the opposite side of the container to determine the absorption of the fluid sample or one or more components of the fluid sample;
f. obtaining data from the sample while the sample remains in the container and using the data to carry out a coagulation study or other chemistry procedure on the sample from the data obtained while the sample was present in the container.

34. A method of conducting coagulation studies and other chemistry procedures on a blood or fluid sample, comprising the steps of:
a. providing a closed sample container having optically clear sides and a covered opening, with the container having therein a thixotropic substance, an anticoagulant and a vacuum pressure corresponding to a predetermined amount of a volume of a fluid to be aspirated into the sample container;
b. aspirating from the body of a patient a sample of a body fluid into the container by puncturing the covered opening;
c. centrifuging the container with the fluid sample of step (b);
d. placing the container with the fluid sample centrifuged in step (c) into a potentiophotometer having at least one emitting light source and at least one detecting cell;
e. scanning the sample in the container with at least one emitting light source positioned on one side of the container and detecting with at least one detector cell positioned on the opposite side of the container to determine the absorption of the fluid sample or one or more components of the fluid sample.

* * * * *